United States Patent [19]

Sircar

[11] 4,351,950
[45] Sep. 28, 1982

[54] ANTI-ARTERIOSCLEROTIC AGENTS

[75] Inventor: Ila Sircar, Ann Arbor, Mich.

[73] Assignee: Warner-Lambert Company, Morris Plains, N.J.

[21] Appl. No.: 108,978

[22] Filed: Jan. 2, 1980

[51] Int. Cl.$^3$ .................................................. C07C 69/76
[52] U.S. Cl. ...................................... 560/62; 560/9;
560/23; 560/53; 560/56; 560/59; 560/61;
562/426; 562/429; 562/431; 562/434; 562/438;
562/466; 562/469; 562/471; 568/39; 568/41;
568/439; 568/440; 568/441; 568/442; 568/633;
568/634; 568/648; 568/649; 424/308; 424/309;
424/331; 424/333; 424/341; 560/11; 560/17

[58] Field of Search .................. 560/59, 61, 62, 9, 11,
560/23, 17, 53, 56, 62; 562/469, 426, 429, 431,
434, 438, 466, 469, 471; 568/442, 41, 39, 648,
649, 439, 440, 441, 633, 634; 424/308, 309, 331,
333, 341

[56] References Cited

U.S. PATENT DOCUMENTS

| 3,446,838 | 5/1969 | Szobel et al. | 560/59 |
| 3,686,271 | 8/1972 | Lefon | 560/59 |
| 3,824,293 | 7/1974 | Brode | 560/17 |

*Primary Examiner*—Paul J. Killos
*Attorney, Agent, or Firm*—Stephen I. Miller

[57] ABSTRACT

Novel substituted arylene compounds and methods for their preparation and use are disclosed. These new compounds are useful as anti-arteriosclerotic agents.

32 Claims, No Drawings

ANTI-ARTERIOSCLEROTIC AGENTS

BACKGROUND OF THE INVENTION

Elevated levels of blood cholesterol and blood lipids are conditions which are believed related to the onset of arteriosclerosis. Thus, compounds capable of reducing the levels of these blood constituents are recognized as potentially useful anti-arteriosclerotic agents. The prior art contains many materials which are characterized as potentially useful anti-arteriosclerotic agents. These agents and intermediates thereto, which applicant believes are most closely structurally related to the compounds of the present invention are as follows:

U.S. Pat. No. 3,686,271 discloses a class of arylene bis alpha-alkyloxyacetic acids and certain derivatives; U.S. Pat. No. 3,769,436 discloses a class of arylenebisoxyaceticacids and certain derivatives.

The compounds of the present invention are certain arylene 2,2-dimethylalkonoic acids and derivatives thereof. The compounds of the formula:

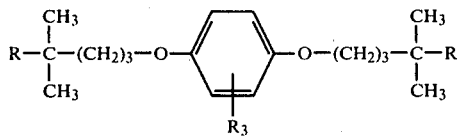

wherein R and $R_3$ are as hereinbelow defined are the preferred compounds of the invention.

The compounds of the present invention are useful as hypocholesterolemic agents and possess the additional advantage of elevating the high density lipoprotein fraction of cholesterol (HDL-cholesterol), which is known to lower the risk factor of coronary heart disease (Gordon, T. et al., High Density Lipoprotein as a Protective Factor Against Coronary Heart Disease, May 1977, The American Journal of Medicine, Vol. 62, pp. 707-714). Certain compounds of the invention also reduce the low density lipoprotein fraction of cholesterol (LDL-cholesterol), thus further reducing the risk factor of coronary heart disease.

SUMMARY OF THE INVENTION

The invention relates to a compound of the formula:

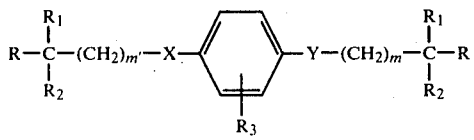

wherein X and Y are the same or different and are oxygen, sulfur, sulfone or sulfoxide; m and m' are the same or different and are integers chosen from 2-5; R is $CH_2OH$; CHO; $CO_2A$ wherein A is hydrogen, alkyl of from 1 to 6 carbon atoms, an alkali or alkaline earth metal cation, an organic amine cation or ammonium; $R_1$ and $R_2$ are the same or different and are alkyl of from 1 to 6 carbon atoms, or when taken together are $-(CH_2)-_{3-5}$; and $R_3$ is hydrogen, halo, alkyl of from 1 to 6 carbon atoms, methoxy, phenyl, trifluoromethyl, 2,5-dichloro, 2,5-dimethyl, 2,3,5-trimethyl, carboxylic acyl of from 1 to 6 carbon atoms, alphahydroxyalkyl of from 1 to 6 carbon atoms, 2-chlorophenyl, 4-chlorophenyl, 2,4-dichlorophenyl, 4-methoxyphenyl, 2-tolyl, 4-tolyl or

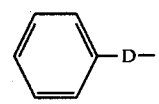

wherein D is $O, CO, S, SO, SO_2, CH_2$, or CHOH; provided that $R_3$ may not be hydrogen when X and Y are oxygen, m and m' are 2, $R_1$ and $R_2$ are $CH_3$, and R is $CO_2H$;

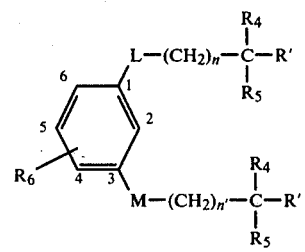

wherein L and M are the same or different and are oxygen, sulfur sulfone or sulfoxide; n and n' are the same or different and are integers chosen from 2-5; $R_4$ and $R_5$ are the same or different and are alkyl of from 1 to 6 carbon atoms; R' is $CH_2OH$; CHO; $CO_2A$ wherein A is hydrogen, alkyl of from 1 to 6 carbon atoms, an alkali or alkaline earth metal cation, an organic amine cation or ammonium; and $R_6$ is hydrogen, 4-formyl, 2-nitro, 2-methyl, 5-methyl, 4-benzoyl or 4-chloro;

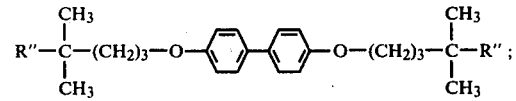

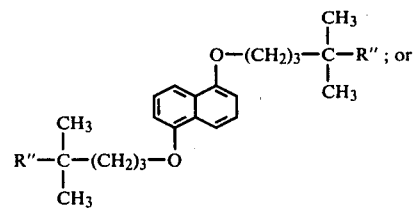

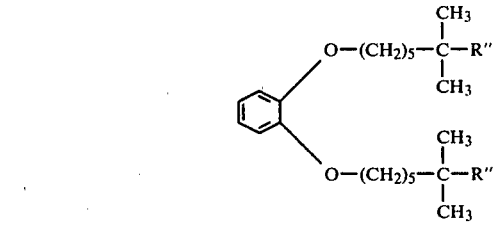

wherein R" is $CH_2OH$; CHO; $CO_2A$ wherein A is hydrogen, alkyl of from 1 to 6 carbon atoms, an alkali or alkaline earth metal cation, an organic amine cation or ammonium.

The invention also relates to processes for preparing the above described compounds.

The invention also relates to methods for using the above described compounds as anti-arteriosclerotic agents for treating mammals.

The invention also relates to pharmaceutical compositions comprising a plasma high density lipoprotein increasing amount of a compound as described above as well as the pharmaceutically acceptable acid-addition salts thereof and mixtures thereof.

DESCRIPTION OF THE INVENTION

The compounds of the invention may be prepared by several methods. These methods, which are equivalent for purposes of the invention, are described hereinbelow with specific reference to the dioxyphenylene compounds of the invention. This description is utilized merely for convenience and those skilled in the art will recognize that the analogous sulfur containing compounds can be prepared by substituting sulfur containing starting materials and utilizing substantially identical reactions or obvious variations thereof. Those skilled in the art will also recognize that the sulfur compounds can be utilized to prepare corresponding sulfone and sulfoxide compounds by art-recognized methods.

In the preferred method of the invention, a compound of the formula I:

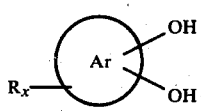

wherein 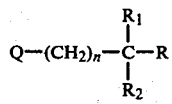 is

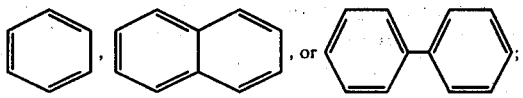

and $R_x$ represents any of the hereinbefore defined substituents $R_3$ and $R_6$, is reacted with a compound (alkylating agent) of the formula II:

wherein n, R, $R_1$ and $R_2$ are as hereinabove defined. In formula I (Ar) is preferably and in formula II n is preferably 3, R is preferably $CO_2CH_3$ and $R_1$ and $R_2$ are preferably $CH_3$.

Q is a substituent known to those skilled in the art as a "leaving group" [C. H. Snyder and A. R. Soto, J. Org. Chem., 30, 673 (1965)]. For purposes of the invention, the halogens are suitable leaving groups and the preferred halogen is bromine. Other suitable leaving groups such as p-toluenesulfonyloxy will be known to those skilled in the art. The reaction is carried out in the presence of a base, examples of which are the alkali-metal hydrides, amides, hydroxides, alkoxides and carbonates such as sodium hydride, potassium amide, potassium hydroxide, sodium methoxide, potassium t-butoxide, sodium carbonate and the like. The preferred bases are the alkali metal hydrides, especially sodium hydride. The reaction is conducted in an anhydrous, non-protic solvent such as an ether, a hydrocarbon or a tertiary amide; examples of such solvents are dimethoxyethane, dioxane, tetrahydrofuran, pentane, cyclohexane, benzene, xylene, and N,N-dimethylformamide. Other suitable solvents will suggest themselves to those skilled in the art. The preferred solvent is N,N-dimethylformamide. The time and temperature ranges for conducting the foregoing reaction may be varied, and in general, a temperature range of about 20° C. to about 70° C. and a time range of about 2 to about 24 hours can be used. The preferred ranges are about 60°–70° C. for about 4–5 hours. The ranges can vary depending on the reactants, the solvent and the base being utilized, and it is within the skill of the art to choose these ranges to optimize the yield for a specific reaction. When carrying out the above-described reaction, it is preferred to use slightly more than two equivalents of the alkylating agent, II, and slightly more than two equivalents of base per mole of the compound, I. The use of a greater excess of base, for example from 4 to 10 equivalents, is desirable when an alkali metal carbonate such as sodium or potassium carbonate is utilized. The product of the reaction, represented by the preferred structure III,

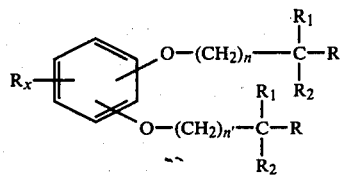

may be isolated by standard procedures, for example, addition of the reaction mixture to water, separating the organic phase when present, extracting the aqueous phase with a water-immiscible solvent such as diethyl ether, washing the combined organic phases with water, drying the washed organic phase with, for example, $MgSO_4$, evaporating the solvent and purifying the product by, for example, vacuum distillation. Alternately, when R is an ester this function may be saponified, with for example, methanolic sodium hydroxide, and the acid product may be isolated and purified by well-known methods. If desired, the ester functions may be saponified after the ester has been isolated and purified. The above described reaction of compounds I and II will produce products, III, wherein n and n' are the same. When it is desired to prepare a compound of formula III wherein n and n' are different, those skilled in the art will understand that the reaction can be performed in two separate stages, i.e., each step utilizing substantially one equivalent of alkylating agent II, and substantially one equivalent of base for each mole of compound I.

The compounds, I, and the alkylating agents, II, are either commercially available or are readily prepared. The preferred alkylating agent, methyl 5-bromo-2,2-dimethylpentanoate may be prepared from 2,2-dimethyl-4pentenoic acid [J.Am.Chem.Soc., 77, 1092 (1955)] by the addition of hydrogen bromide in the presence of benzoyl peroxide.

A second method for preparing the compounds of the invention comprises the reaction of an arylenebis(oxy)alkyl compound of formula IV:

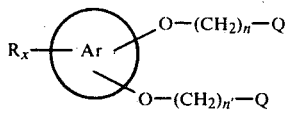

wherein $\widehat{Ar}$, n, n', $R_x$ and Q are as previously defined with a compound of formula V:

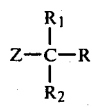

wherein R, $R_1$ and $R_2$ are as previously defined. Z is an alkali metal which is preferably lithium, R is preferably $CO_2A'$, wherein A' is sodium or lithium, and $\widehat{Ar}$ is preferably

Preferred solvents for use in this reaction are anhydrous polar solvents such as tetrahydrofuran, tetrahydropyran, dimethoxy ethane, diethylene glycol dimethyl ether and dimethyl sulfoxide. Tetrahydrofuran is the preferred solvent at temperatures, up to about 40° C. whereas diethylene glycol dimethyl ether is the preferred solvent at temperatures above 40° C. The reaction solvent can also be a hydrocarbon such as pentane, heptane, benzene or toluene, as well as mixtures thereof.

The time and temperature for conducting the reaction are dependent on the particular reactants and the solvent that is used. In general a temperature from about $-10°$ C. to about 60° C. and a reaction time of from about one hour to about 24 hours can be used. According to the preferred method, the reaction is carried out at a temperature between 0° C. to about 30° C. for about 16 hours. When reacting compounds IV and V, a ratio of 2 equivalents of V to 1 mole of IV is normally utilized, but it is preferred to use a slight excess of the arylenebis(oxy)alkyl compound, IV.

The product may be isolated and purified by standard procedures, such as those described hereinabove for compound III. When the product is in the form of the diester, it may be saponified, if desired, for example with dilute base either before or after its isolation and purification. The starting arylenebis(oxy)alkyl compounds, IV, may be prepared by well-known methods such as by reaction of the corresponding compound, I, with a compound of the formula VI [R. Adams and L. N. Whitehall, J. Am. Chem. Soc., 63, 2073 (1949)],

wherein Q and Q' are leaving groups which may be the same or different and are defined hereinabove, n is also as previously defined. For purposes of the invention, Q and Q' are preferably different, for example Q may be chlorine when Q' is bromine. The reaction of compound I with VI is performed in substantially the same manner as that described hereinabove for the reaction of compound II with compound I.

Certain of the compounds may be prepared by aromatic ring substitution. Thus, the benzene ring of a compound of formula III wherein $\widehat{Ar}$ is

and $R_x$ is hydrogen may be, for example, halogenated.

The compounds of the invention wherein R is CHO may be prepared by reduction of the corresponding acid or by oxidation of the corresponding alcohol. These compounds can also be prepared by using starting materials such as II or V wherein R is a protected CHO group such as in the form of an ethylene acetal. The protecting group is subsequently removed, for example, by dilute acid hydrolysis of the ethylene acetal.

The compounds of the invention wherein R is $CH_2OH$ can also be prepared from the corresponding aldehyde, free acid or ester by, for example, reduction with lithium aluminum hydride. The carboxylic acids of the invention, i.e., the compounds of formula III wherein R, R' and R'' are $CO_2H$, form carboxylate salts with any of a variety of inorganic and organic bases. Suitable bases for purposes of the invention, are those which form pharmaceutically-acceptable salts such as sodium hydroxide, sodium carbonate, sodium bicarbonate, potassium hydroxide, calcium hydroxide, ammonia and amines. The salts are converted back to their respective carboxylic acids by treatment with an acid such as dilute hydrochloric acid. The carboxylic acids and their respective salts differ in certain physical properties such as solubility properties but they are otherwise equivalent for purposes of the invention.

The compounds of the invention can exist in unsolvated as well as solvated forms, including hydrated forms. In general, these solvated forms with pharmaceutically acceptable solvents such as water, ethanol and the like are equivalent to the unsolvated forms for purposes of the invention.

The compounds of the invention are new chemical substances, of value as pharmacological agents which increase the high density lipoprotein fraction of cholesterol (HDL-cholesterol) at the expense of the low density lipoprotein fraction of cholesterol (LDL-cholesterol). In addition, many of the compounds of the invention reduce total plasma cholesterol levels. The risk of coronary heart disease is thereby reduced. The effectiveness of the compounds of the invention was established by the screening procedure described in Maxwell, R. E., Nawrocki, J. W., and Uhlendorf, P. D., Artery, 4, 303 (1978).

A compound is considered active in this procedure if it increases the HDL fraction of cholesterol by at least 50%. The test results obtained for compounds of the invention are shown in the following table.

| | | TEST RESULTS | | |
| | | Percent Change | | |
| Compound of Example | Dose mg/kg | Plasma Cholesterol | HDL Cholesterol | HDL/LDL Electro-Phoretic |
|---|---|---|---|---|
| 1A | 50 | −30 | 347 | 435 |

-continued

TEST RESULTS

| Compound of Example | Dose mg/kg | Percent Change Plasma Cholesterol | HDL Cholesterol | HDL/LDL Electro- Phoretic |
| --- | --- | --- | --- | --- |
| 1B | 50 | 0 | 381 | 318 |
| 1D | 50 | −30 | 385 | 595 |
| 1G | 50 | 0 | 480 | — |
| 1K | 50 | 0 | 628 | — |
| 1M | 50 | 0 | 674 | — |
| 1O | 50 | 0 | 723 | — |
| 1P | 50 | +39 | 1100 | — |
| 1Q | 50 | 0 | 421 | — |
| 1R | 50 | −30 | 686 | — |
| 1S | 50 | +32 | 428 | — |
| 2 | 50 | −26 | 566 | 871 |
| 2A | 50 | −37 | 743 | 1009 |
| 2B | 50 | −45 | 728 | 1311 |
| 4 | 50 | −27 | 1410 | 2432 |
| 4 | 25 | — | 741 | 1798 |
| 4 | 12.5 | — | 518 | 945 |
| 5 | 50 | −45 | 791 | 2472 |
| 5A | 50 | 0 | 1477 | 1722 |
| 5D | 50 | −55 | 384 | 1091 |
| 5E | 50 | −62 | 348 | 377 |
| 5F | 50 | −53 | 753 | 1443 |
| 5F | 25 | — | 206 | 493 |
| 5F | 12.5 | — | 94 | 242 |
| 5I | 50 | −52 | 294 | 794 |
| 5J | 50 | −28 | 383 | 510 |
| 5K | 50 | −37 | 317 | 556 |
| 5L | 50 | 0 | 276 | 274 |
| 5M | 50 | −44 | 628 | 785 |
| 5M | 25 | — | 232 | 302 |
| 5M | 12.5 | — | 74 | 101 |
| 6 | 50 | −33 | 289 | 388 |
| 7 | 50 | 0 | 907 | 703 |
| 8 | 50 | −27 | 525 | 509 |
| 10 | 50 | −44 | 389 | — |
| 11 | 50 | — | 410 | — |
| 12 | 50 | +40 | 319 | — |
| 13 | 50 | +61 | 1292 | — |
| 14 | — | — | — | — |
| 17 | 50 | 0 | 947 | — |

The compounds of the invention can be administered either orally or parenterally. They can be combined with a solid or liquid carrier or diluent and made available in varying amounts in such pharmaceutical forms as tablets, capsules, powders, and aqueous and non-aqueous suspensions and solutions. The preferred daily dosage is from about 10 to about 250 mg/kg which may be administered in either single or divided dosage units.

The starting materials for preparing the compounds of the invention are either commercially available or can be readily prepared by published literature procedures, for example: 2,5-Dioxybenzophenone is prepared according to J. Herzig and Br. Hofmann, Ber, 41, 143 (1908); Phenylthio-benzohydroquinone is prepared according to O. Dimroth, L. Kraft, and K. Aichinger, Ann. der Chemie, 545, 124 (1940). All the substituted phenylhydroquinones are prepared according to D. E. Kvalnes, J. Am. Chem. Soc., 56, 2478 (1934). Fluorohydroquinone and trifluoromethylhydroquinone are prepared according to the procedure of A. E. Feiring, and W. A. Sheppard, J. Org. Chem., 40, 2543 (1975).

The invention is illustrated by the following examples.

EXAMPLE 1

A solution of 3.32 g of t-butylhydroquinone in 15 ml of dimethylformamide is added dropwise to a suspension of 2.4 g of 50% sodium hydride in 25 ml of dimethylformamide, and allowed to stir for ½ an hour at room temperature. 11.2 g of methyl 5-bromo-2,2-dimethylpentanoate is added followed by heating the mixture at 60°–70° C. for 6 hrs. Dimethylformamide is distilled off, the residue is poured into water and the organic material is extracted with ether. The ether extract is washed with water until neutral, dried over anhydrous magnesium sulfate and the ether is evaporated. The residue is purified by distillation yielding the product, dimethyl 5,5'-[[2-(1,1-dimethylethyl)1,4-phenylene]bis(oxy)]-bis[2,2-dimethylpentanoate] b.p. 200° C. at 0.5 mm of Hg; yield 4 g.

Following the general procedure of Example 1, with the substitution of an equivalent amount of the specified diphenol, the following products are obtained:

A. From fluorohydroquinone, the product obtained is dimethyl 5,5'-[(2-fluoro-1,4-phenylene)bis(oxy)]-bis[2,2-dimethylpentanoate], m.p. 33°–35° following crystallization from ether-petroleum ether.

B. From 2,5-dihydroxyacetophenone, the product obtained is dimethyl 5,5'-[(2-acetyl-1,4-phenylene)bis-(oxy)]bis[2,2-dimethylpentanoate] b.p. 210° C. at 0.1 mm of Hg.

C. From 2,4-dihydroxybenzophenone, the product obtained is dimethyl 5,5'-[(4-benzoyl-1,3-phenylene)bis-(oxy)]bis[2,2-dimethylpentanoate], which is hydrolysed directly by refluxing with a solution of 2 N methanolic sodium hydroxide to give the corresponding acid, 5,5'-[(4-benzoyl-1,3-phenylene)bis(oxy)[bis-[2,2-dimethylpentanoic acid] m.p. 125°–126° C., following crystallization from tetrahydrofuran-isopropyl ether.

D. From 2-methylresorcinol, the product obtained is dimethyl 5,5'-[(2-methyl-1,3-phenylene)bis(oxy)]bis[2,2-dimethylpentanoate], b.p. 200° C. at 0.3 mm of Hg.

E. From 5-methylresorcinol, the product obtained is dimethyl 5,5'-[(5-methyl-1,3-phenylene)bis[2,2-dimethylpentanoate], b.p. 200° C. at 0.3 mm of Hg.

F. From 4-chlorobenzene 1,3-dithiol the product obtained is dimethyl 5,5'-[(4-chloro-1,3-phenylene)bis(-thio)]bis[2,2-dimethylpentanoate] b.p. 200° C. at 0.02 mm of Hg.

G. From o-chlorophenylhydroquinone, the product obtained is 5,5'-[2'-chloro[1,1'-biphenyl]-2,5-diyl)bis(oxy)]bis[2,2-dimethylpentanoic acid], m.p. 101°–2° C., following crystallization from isopropyl ether.

H. From p-anisylhydroquinone, the product obtained is 5,5'-[(4'-methoxy[1,1'-biphenyl]-2,5-diyl)bis(oxy)]-bis[2,2-dimethylpentanoic acid[, m.p. 69°–73° (d), following crystallization from isopropyl ether.

I. From p-chlorophenylhydroquinone, the product obtained is 5,5'-[(4'-chloro[1,1'-biphenyl]-2,5-diyl)bis-(oxy)]bis[2,2-dimethylpentanoic acid], m.p. 110°–111° C., following crystallization from tetrahydrofuran-petroleum ether.

J. From p-tolylhydroquinone, the product obtained is 5,5'-[(4'-methyl[1,1-biphenyl]-2,5-diyl)bis(oxy)]bis[2,2-dimethylpentanoic acid[, m.p. 65°–8° C., following crystallization from chloroform.

K. From o-tolylhydroquinone, the product obtained is 5,5'-[(2'-methyl[1,1'-biphenyl]2,5-diyl)bis(oxy)]-bis(2,2-dimethylpentanoic acid), m.p. 65°–8° C., following crystallization from isopropyl ether.

L. From 2,5-dihydroxybenzaldehyde, the product obtained is dimethyl 5,5'-[(2-formyl-1,4-phenylene)bis-(oxy)[bis[2,2-dimethylpentanoate], b.p. 220° C. at 0.1 mm of Hg.

M. From trifluoromethylhydroquinone, the product obtained is 5,5'-[(2-trifluoromethyl-1,4-phenylene)bis- (oxy)]bis[2,2-dimethylpentanoic acid], m.p. 114°–5° C., following crystallization from tetrahydrofuran-hexane.

N. From 2,4-dichlorophenylhydroquinone, the product obtained is 5,5'-[2',4'-dichloro[1,1-biphenyl]2,5-dilyl)bis(oxy)]bis[2,2-dimethylpentanoic acid], m.p. 82°–6° C., following crystallization from isopropyl ether.

O. From 2,5-dihydroxypropiophenone, the product obtained is dimethyl 5,5'-[[2-(1-oxopropyl)-1,4-phenylene]bis(oxy)]bis[2,2-dimethylpentanoate].

P. From 2,5-dihydroxybutyrophenone, the product obtained is dimethyl 5,5'-[[2-(1-oxobutyl)-1,4-phenylene]bis(oxy)]bis[2,2-dimethylpentanoate].

Q. From 2,5-dihydroxybenzophenone, the product obtained is dimethyl 5,5'-[(2-benzoyl-1,4-phenylene)bis(oxy)]bis[2,2-dimethylpentanoate].

R. From 2,5-dimethylhydroquinone, the product obtained is dimethyl 5,5'[2,5-dimethyl-1,4-phenylebis(oxy)]bis[2,2-dimethylpentanoate], m.p. 60°–2° C., following crystallization from isopropyl ether.

S. From phenylthiobenzohydroquinone, the product obtained is 5,5'-[(2-phenylthio)-1,4-phenylene)bis(oxy)]-bis[2,2-dimethylpentanoic acid], m.p. 117°–8° C., following crystallization from tetrahydrofuran-isopropyl ether.

EXAMPLE 2

A solution of 3.5 g of 2-methoxyhydroquinone in 35 ml of methanol is stirred with 3.0 g of sodium methoxide for thirty minutes. 12.3 g of methyl 5-bromo-2,2-dimethylpentanoate is added and the mixture is refluxed for 24 hours. Methanol is removed under reduced pressure and the residue is poured into water. An oil separates, which is extracted with ether and the ether extract is washed with water, dried over anhydrous magnesium sulfate and the ether is evaporated. The residue is purified by distillation yielding the product, dimethyl 5,5'-[(2-methoxy-1,4-phenylene)bis(oxy)]bis[2,2-dimethylpentanoate] b.p. 200° C. at 0.2 mm of Hg; yield 6.6 g.

Following the general procedure of Example 2, with the substitution of an equivalent amount of the specified diphenol, the following products are obtained:

A. From methylhydroquinone the product obtained is dimethyl 5,5'-[(2-methyl-1,4-phenylene)bis(oxy)]-bis[2,2-dimethylpentanoate] b.p. 192° C. at 0.15 mm of Hg.

B. From bromohydroquinone, the product obtained is dimethyl 5,5'[(2-bromo-1,4-phenylene)bis(oxy)]bis [2,2-dimethylpentanoate] b.p. 200° C. at 0.3 mm of Hg.

EXAMPLE 3

A suspension of 3.45 g of 2,4-dihydroxybenzaldehyde, 10.4 g of anhydrous potassium carbonate, 0.5 g of potassium iodide and 13.4 g of methyl 5-bromo-2,2-dimethylpentanoate in 70 ml of acetone is refluxed for 24 hours. The suspension is cooled, filtered and the solvent is evaporated. The residue is poured into water, and the organic material is extracted with ether. The ether extract is washed with water, dried over anhydrous magnesium sulfate and evaporated. The residue is purified by distillation yielding the product, dimethyl 5,5'-[(4-formyl-1,3-phenylene)bis(oxy)]bis[2,2-dimethylpentanoate], b.p. 210° C. at 0.1 mm of Hg; yield 6.5 g.

A. From 2-nitroresorcinol the product obtained is dimethyl 5,5'-[(2-nitro-1,4-phenylene)bis(oxy)]bis[2,2-dimethylpentanoate] b.p. 230° C. at 1.0 mm of Hg.

B. From 4,4'-biphenyldithiol, the product obtained is dimethyl 5,5'-[[1,1'-biphenyl]-4,4'-diylbis(thio)]bis[2,2-dimethylpentanoate], m.p. 46°–7°, following crystallization from isopropyl ether.

EXAMPLE 4

A solution of 60.0 g of phenylhydroquinone in 200 ml of dimethylformamide is added dropwise to a suspension of 27.5 g of 59% sodium hydride in 100 ml of dimethylformamide with stirring under $N_2$ blanket. The mixture is stirred for one hour at room temperature to complete the reaction. One hundred fifty-six ml of methyl 5-bromo-2,2-dimethylpentanoate is added dropwise at room temperature followed by heating the mixture at 80°–85° C. for 12–14 hours. The mixture is cooled, filtered from the inorganic residue and dimethylformamide is distilled under reduced pressure. The residue is treated with water and the organic material is extracted with ether. The ether extract is dried over anhydrous magnesium sulfate and ether removed leaving behind an oil. The unreacted alkyl bromide is removed by distillation under high vacuum and the residue is purified by chromatography over silica gel. The crude diester (160 g) is directly hydrolyzed by refluxing with 1600 ml of 2 N methanolic sodium hydroxide for 3 hours. Methanol is removed and the residue is treated with water followed by acidification. The product obtained is 5,5'-[(1,1'-biphenyl)-2,5-diylbis(oxy)]bis[2,2-dimethylpentanoic acid], mp 139°–140° C., following crystallization from tetrahydrofuran-isopropyl ether, yield 125 g.

EXAMPLE 5

17.6 g of isobutyric acid is added dropwise to a stirred suspension of 10.6 g of 50% NaH and 20.6 g of diisopropylamine in 170 ml of anhydrous tetrahydrofuran at room temperature under nitrogen. The mixture is refluxed for 30 minutes followed by cooling to 0° C. At this time 138 ml of a solution of butyllithium in heptane is added slowly. The ice-bath is retained for 30 minutes followed by warming to 30°–40° for another 30 minutes. The slightly turbid solution is cooled to 0° C. and a solution of 26.3 g of 1,4-bis(3-chloropropoxy)benzene in 50 ml of dry tetrahydrofuran is added dropwise while the temperature was maintained below 10° C. After 30 minutes the mixture is allowed to warm to room temperature and stirring is continued for 16 hours. The mixture is cooled and hydrolysed with 250 ml of water and the aqueous phase is separated, washed with 100 ml of ether, and acidified with 6 N hydrochloric acid yielding the product, 5,5'-[1,4-phenylenebis(oxy)]bis[2,2-dimethyl pentanoic acid], m.p. 168° C., following crystallization from tetrahydrofuranisopropyl ether, yield 23 g.

Following the general procedure of Example 5, with the substitution of an equivalent amount of the specified starting material the following products are obtained:

A. From 1,4-bis(4-chlorobutoxy)benzene the product obtained is 6,6'-[1,4-phenylenebis(oxy)]bis[2,2-dimethylhexanoic acid], m.p. 158°–159° C. following crystallization from tetrahydrofuran-hexane.

B. From cyclobutane carboxylic acid the product obtained is 1,1'-[1,4-phenylenebis[oxy(4,1-obtained is 1,1'-[1,4-phenylenebis[oxy(4,1-butanediyl)]]biscyclobutanecarboxylic acid, m.p. 132°–133° C. following crystallization from tetrahydrofuran-petroleum ether.

C. From 1,4 bis(3-chloropropoxy)2,3,5-trimethylbenzene the product obtained is 5,5'-[(2,3,5-trimethyl-1,4-phenylene)bis(oxy)]bis[2,2-dimethylpentanoic acid], m.p. 143° C. following crystallization from diethyl ether.

D. From 1,4 bis(3-chloropropoxy)2,5 dichlorobenzene, the product obtained is 5,5'-[(2,5-dichloro-1,4-phenylene)bis(oxy)]bis[2,2-dimethylpentanoic acid], m.p. 162° C. following crystallization from tetrahydrofuran-isopropyl ether.

E. From 1,4 bis(2-chloroethoxy)-2-chlorobenzene, the product obtained is 4,4'-[(2-chloro-1,4-phenylene)bis (oxy)]bis[2,2-dimethylbutanoic acid], m.p. 135°–137° C. following crystallization from tetrahydrofuran-isopropyl ether.

F. From 1,4 bis(3-chloropropoxy)-2-chlorobenzene, the product obtained is 5,5'-[(2-Chloro-1,4-phenylene)-bis (oxy)]bis[2,2-dimethylpentanoic acid], m.p. 135° C. following crystallization from tetrahydrofuran-isopropyl ether.

G. From 4,4'-bis(3-chloropropoxy)1,1'-biphenyl, the product obtained is 5,5-[(1,1'-biphenyl)-4,4'-diylbis(oxy)]bis[2,2-dimethylpentanoic acid], m.p. 201° C., following crystallization from tetrahydrofuranhexane.

H. From 1,5-bis(3-chloropropoxy)naphthalene, the product obtained is 5,5'-[1,5-naphthalene-diylbis(oxy)]-bis[2,2-dimethylpentanoic acid], m.p. 219° C. following crystallization from dimethylformamide.

I. From 1,3 bis(3-chloropropoxy)benzene, the product obtained is 5,5'-[1,3-phenylenebis(oxy)]bis[2,2-dimethylpentanoic acid], m.p. 135°–136° C., following crystallization from isopropyl ether.

J. From 1,3 bis(2-chloroethoxy)benzene, the product obtained is 4,4'-[1,3-phenylenebis(oxy)]bis[2,2-dimethylbutanoic acid], m.p. 104°–105° C., following crystallization from diethyl ether-petroleum ether.

K. From 1,3 bis(4-chlorobutoxy)benzene, the product obtained is 6,6'-[1,3-phenylenebis(oxy)]bis[2,2-dimethylhexanoic acid], m.p. 85°–86° C., following crystallization from isopropyl ether.

L. From 1,2 bis(5-chloropentoxy)benzene, the product obtained is 7,7'-[1,2-phenylenebis(oxy)]bis[2,2-dimethylheptanoic acid], m.p. 61° C., following crystallization from diethyl ether-petroleum ether.

M. From 1-(3-chloropropoxy)-4-[(3-chloropropyl)-thio]benzene, the product obtained is 5-[(4-[(4-carboxy-4-methylpentyl)oxyl]phenyl)thio]-2,2-dimethylpentanoic acid, m.p. 112° C. following crystallization from chloroform-petroleum ether.

EXAMPLE 6

A solution of 3.05 g of 5-[[4-(4-carboxy-4-methylpentyl)oxy]-2,5-dimethylphenyl]thio]-2,2-dimethylpentanoic acid in 10 ml of glacial acetic acid containing 0.9 ml of hydrogen peroxide is stirred at room temperature for 6 hrs. The solution is poured into water and extracted with ether. The ether extract is washed with water, dried over anhydrous magnesium sulfate and the solvent is evaporated. The residual oil solidifies on trituration with isopropyl ether and the product obtained is 5-[[4-[(4-carboxy-4-methylpentyl)oxy]phenyl]sulfinyl]-2,2-dimethylpentanoic acid, m.p. 98°–100° C., following crystallization from tetrahydrofuran-isopropyl ether; yield 1.9 g.

EXAMPLE 7

A solution of 6.56 g of 6,6'-[1,4-phenylene bis(oxy)]-bis[2,2-dimethylhexanoic acid] in 25 ml of tetrahydrofuran is added to a stirred suspension of 1.1 g of lithium aluminum hydride in 75 ml of tetrahydrofuran followed by refluxing for 5–6 hours. The mixture is cooled, and the excess hydride is decomposed with saturated sodium sulfate solution, filtered from the inorganic solids and the filtrate is evaporated. The product obtained is, 6,6'-[1,4-phenylenebis(oxy)]bis[2,2-dimethyl-1-hexanol], m.p. 72° C. following crystallization from tetrahydrofuran-hexane, yield 4 g.

EXAMPLE 8

4.0 g of dimethyl 5,5'-[(1-acetyl-1,4-phenylene)bis(oxy)]bis[2,2-dimethylpentanoate]is treated with 0.4 g of sodium borohydride in 40 ml of methanol at room temperature. After usual workup, the residue is hydrolysed with 2 N methanolic sodium hydroxide yielding the product, 5,5'-[2-(hydroxyethyl)-1,4-phenylenebis(oxy)]-bis[2,2-dimethylpentanoic acid], m.p. 141°–143° C., following crystallization from tetrahydrofuranisopropyl ether, yield 1.2 g.

EXAMPLE 9

A solution of 2.5 g of dimethyl 5,5'-[[2-(1-hydroxypropyl)-1,4-phenylene]bis(oxy)]bis[2,2-dimethylpentanoate] in 25 ml of benzene was refluxed 8 hrs in the presence of catalytic amount of p-toluenesulfonic acid. After usual work up, the product obtained is dimethyl 5,5'-[2-(1-propenyl)1,4-phenylenebis(oxy)]bis[2,2-dimethylpentanoate], yield 1.1 g.

EXAMPLE 10

3.0 g of dimethyl 5,5'-[(2-benzoyl-1,4-phenylene)bis-(oxy)]bis[2,2-dimethylpentanoate] is reduced catalytically and the crude ester saponified. The product thus obtained is 5,5'-[[2-(benzyl)-1,4-phenylene]bis(oxy)]-bis[2,2-dimethylpentanoic acid], m.p. 140°–141° C. following crystallization from tetrahydrofuran-petroleum ether, yield 2.1 g.

EXAMPLE 11

A solution of 2.09 of dimethyl 5,5'-[(2-benzoyl-1,4-phenylene)bis(oxy)]bis[2,2'-dimethylpentanoate] in 20 ml of 95% alcohol is refluxed with 2.0 g of Zn-dust and 2.0 g of sodium hydroxide. The suspension is filtered, acidified, and the product obtained is 5,5'-[2-(hydroxyphenylmethyl)-1,4-phenylenebis(oxy)]bis[2,2-dimethylpentanoic acid], m.p. 125°–128° C., following crystallization from ether hexane, yield 1 g.

EXAMPLE 12

3.8 g of dimethyl 5,5'-[(2-formyl-1,4-phenylene)bis-(oxy)]bis[2,2-dimethylpentanoate] is treated with 0.5 g of sodium borohydride in 40 ml of methanol at room temperature. After usual work up, the residue is hydrolysed with 2 N methanolic sodium hydroxide and the product obtained is 2.7 g of 5,5'-[(2-hydroxymethyl)-1,4-phenylenebis(oxy)]bis[2,2-dimethylpentanoic acid], m.p. 128°–9° C., following crystallization from tetrahydrofuran-isopropyl ether, yield 2.7 g.

EXAMPLE 13

3.65 g of dimethyl 5,5'-[[2-(1-oxobutyl)-1,4-phenylene]bis(oxy)]bis[2,2-dimethylpentanoate] is reduced with 0.5 g of sodium borohydride in 40 ml of methanol at room temperature. After usual work up, the residue is hydrolysed with 2 N methanolic sodium hydroxide and the product obtained is 5,5'-[[2-(1-hydroxybutyl)-1,4-phenylene]bis(oxy)[2,2-dimethylpentanoic acid], m.p. 122°–123° C., following crystallization from ether-isopropyl ether, yield 2.1 g.

EXAMPLE 14

A solution of 2.8 g of 5,5'-[(2-phenylthio)-1,4-phenylene]bis(oxy)]bis[2,2-dimethylpentanoic acid] in 25 ml of methylene chloride is stirred overnight with 1.0 g of m-chloroperbenzoic acid at room temperature. The separated solid is filtered, washed with methylene chloride and dried. The product obtained is 5,5'-[[2-(phenylsulfinyl)-1,4-phenylene]bis(oxy)]bis-[2,2-dimethylpentanoic acid], m.p. 141°–3° C., following crystallization from tetrahydrofuran-isopropyl ether, yield 1.3 g.

EXAMPLE 15

2.4 g of 5,5'-[(2-(phenylthio)-1,4-phenylene]bis(oxy)]-bis[2,2-dimethylpentanoic acid] is treated with 1.8 g of m-chloroperbenzoic acid in 75 ml of methylene chloride. The product obtained is 5,5'-[[2-(phenylsulfonyl)-1,4-phenylene]bis(oxy)]bis[2,2-dimethylpentanoic acid], m.p. 194°–6° C., following crystallization from tetrahydrofuran-isopropyl ether, yield 1.8 g.

EXAMPLE 16

A solution of 4.77 g of 5-[[4-[(4-carboxy-4-methylpentyl)oxy]-2,5-dimethylphenyl]thio]-2,2-dimethylpentanoic acid in 20 ml of glacial acetic acid is treated with 4.9 ml of 30% hydrogen peroxide at 50° C. in three portions followed by refluxing for two hours. The solution is poured into water and the solids are filtered, washed with water and dried. The product obtained is 5-[[4-[(4-carboxy-4-methylpentyl)-oxy]phenyl]sulfonyl]-2,2-dimethylpentanoic acid, m.p. 106°–7° C., following crystallization from tetrahydrofuran-isopropyl ether, yield 4.3 g.

EXAMPLE 17

8.2 g of dimethyl 5,5'-[[2-(1-oxopropyl)-1,4-phenylene]bis(oxy)]bis[2,2-dimethylpentanoate] is treated with 0.85 g of sodium-borohydride in 40 ml of methanol at room temperature. After usual work up, the residue is hydrolysed with 2 N methanolic sodium hydroxide and the product is 5,5'-[2-(1-hydroxypropyl)-1,4-phenylenebis(oxy)]bis[2,2-dimethylpentanoic acid], m.p. 112°–113° C., following crystallization from tetrahydrofuran-petroleum ether, yield 4.1 g.

I claim:
1. A compound having the structural formula:

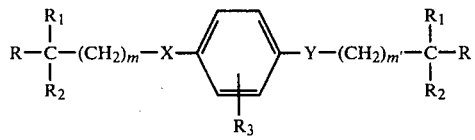

wherein X and Y are the same or different and are oxygen, sulfur, sulfone or sulfoxide; m and m' are the same or different and are integers chosen from 2–5; R is $CH_2OH$; CHO; $CO_2A$ wherein A is hydrogen, alkyl of from 1 to 6 carbon atoms, an alkali or alkaline earth metal cation, an organic amine cation or ammonium; $R_1$ and $R_2$ are the same or different and are alkyl of from 1 to 6 carbon atoms, or when taken together are —($CH_2$)—$_{3-5}$; and $R_3$ is hydrogen, halo, alkyl of from 1 to 6 carbon atoms, methoxy, phenyl, trifluoromethyl, 2,5-dichloro, 2,5-dimethyl, 2,3,5-trimethyl, carboxylic acyl of from 1 to 6 carbon atoms, alpha-hydroxyalkyl of from 1 to 6 carbon atoms, 2-chlorophenyl, 4-chlorophenyl, 2,4-dichlorophenyl, 4-methoxyphenyl, 2-tolyl, 4-tolyl or

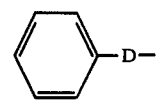

wherein D is $O, CO, S, SO, SO_2, CH_2$, or CHOH; provided that $R_3$ may not be hydrogen when X and Y are oxygen, m and m' are 2; $R_1$ and $R_2$ are $CH_3$, and R is $CO_2H$; and further provided that $R_3$ may not be halo when X and Y are both sulfur; and when R is COOH, the pharmaceutically acceptable salts thereof.

2. The compound as defined in claim 1 which is dimethyl 5,5'-[(2-fluoro-1,4-phenylene)bis(oxy)]bis[2,2-dimethylpentanoate].

3. The compound as defined in claim 1 which is dimethyl 5,5'-[(2-acetyl-1,4-phenylene)bis(oxy)]bis[2,2-dimethylpentanoate].

4. The compound as defined in claim 1 which is 5,5'-[(2'-chloro[1,1'-biphenyl]-2,5-diyl)bis(oxy)]bis[2,2-dimethylpentanoic acid].

5. The compound as defined in claim 1 which is 5,5'-[(2'-methyl[1,1'-biphenyl]2,5-diyl)bis(oxy)]-bis(2,2-dimethylpentanoic acid].

6. The compound as defined in claim 1 which is 5,5'-[(2-trifluoromethyl-1,4-phenylene)bis(oxy)]bis[2,2-dimethylpentanoic acid].

7. The compound as defined in claim 1 which is dimethyl 5,5'-[[2-(1-oxopropyl)-1,4-phenylene]bis(oxy)]-bis[2,2-dimethylpentanoate].

8. The compound as defined in claim 1 which is dimethyl 5,5'-[[2-(1-oxobutyl)-1,4-phenylene]bis(oxy)]-bis[2,2-dimethylpentanoate].

9. The compound as defined in claim 1 which is dimethyl 5,5'-[(2-benzoyl-1,4-phenylene)bis(oxy)]bis[2,2-dimethylpentanoate].

10. The compound as defined in claim 1 which is dimethyl 5,5'[2,5-dimethyl-1,4-phenylebis(oxy)]bis[2,2-dimethylpentanoate].

11. The compound as defined in claim 1 which is 5,5'-[(2-phenylthio)-1,4-phenylene)bis(oxy)]bis[2,2-dimethylpentanoic acid].

12. The compound as defined in claim 1 which is dimethyl 5,5'-[(2-methoxy-1,4-phenylene)bis(oxy)]-bis[2,2-dimethylpentanoate].

13. The compound as defined in claim 1 which is dimethyl 5,5'-[(2-methyl-1,4-phenylene)bis(oxy)]bis[2,2-dimethylpentanoate].

14. The compound as defined in claim 1 which is dimethyl 5,5'[(2-bromo-1,4-phenylene)bis(oxy)]bis[2,2-dimethylpentanoate].

15. The compound as defined in claim 1 which is 5,5'-[(1,1'-biphenyl)-2,5-diylbis(oxy)]bis[2,2-dimethylpentanoic acid].

16. The compound as defined in claim 1 which is 5,5'-[1,4-phenylenebis(oxy)]bis[2,2-dimethyl pentanoic acid].

17. The compound as defined in claim 1 which is 6,6'-[1,4-phenylenebis(oxy)]bis[2,2-dimethylhexanoic acid].

18. The compound as defined in claim 1 which is 5,5'-[(2,5-dichloro-1,4-phenylene)bis(oxy)]bis[2,2-dimethylpentanoic acid].

19. The compound as defined in claim 1 which is 4,4'-[(2-chloro-1,4-phenylene)bis(oxy)]bis[2,2-dimethylbutanoic acid].

20. The compound as defined in claim 1 which is 5,5'-[(2-Chloro-1,4-phenylene)bis(oxy)]bis[2,2-dimethylpentanoic acid].

21. The compound as defined in claim 1 which is 5-[(4-[(4-carboxy-4-methylpentyl)oxy]phenyl)thio]-2,2-dimethylpentanoic acid.

22. The compound as defined in claim 1 which is 5-[[4-[(4-carboxy-4-methylpentyl)oxy]phenyl]sulfinyl]-2,2-dimethylpentanoic acid.

23. The compound as defined in claim 1 which is 6,6'-[1,4-phenylenebis(oxy)bis[2,2-dimethyl-1-hexanol].

24. The compound as defined in claim 1 which is 5,5'-[2-(hydroxyethyl)-1,4-phenylenebis(oxy)]bis[2,2-dimethylpentanoic acid].

25. The compound as defined in claim 1 which is 5,5'-[[2-(benzyl)-1,4-phenylene]bis(oxy)]bis[2,2-dimethylpentanoic acid].

26. The compound as defined in claim 1 which is 5,5'-[2-(hydroxyphenylmethyl)-1,4-phenylenebis(oxy)]-bis[2,2-dimethylpentanoic acid].

27. The compound as defined in claim 1 which is 5,5'-[(2-hydroxymethyl)-1,4-phenylenebis(oxy)]bis[2,2-dimethylpentanoic acid].

28. The compound as defined in claim 1 which is 5,5'-[[2-(1-hydroxybutyl)-1,4-phenylene]bis(oxy)]-bis[2,2-dimethylpentanoic acid].

29. The compound as defined in claim 1 which is 5,5'-[[2(phenylsulfinyl)-1,4-phenylene]bis(oxy)]bis-[2,2-dimethylpentanoic acid].

30. The compound as defined in claim 1 which is 5,5'-[2-(1-hydroxypropyl)-1,4-phenylenebis(oxy)]-bis[2,2-dimethylpentanoic acid].

31. A pharmaceutical composition comprising an anti-artereosclerotic effective amount of a compound having the structural formula:

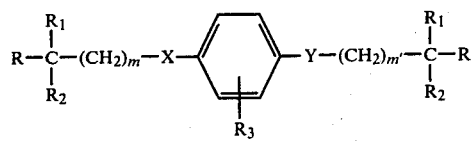

wherein X and Y are the same or different and are oxygen, sulfur, sulfone or sulfoxide; m and m' are the same or different and are integers chosen from 2-5; R is $CH_2OH$; CHO; $CO_2A$ wherein A is hydrogen, alkyl of from 1 to 6 carbon atoms, an alkali or alkaline earth metal cation, an organic amine cation or ammonium; $R_1$ and $R_2$ are the same or different and are alkyl of from 1 to 6 carbon atoms, or when taken together are $-(CH_2)-3-5$; and $R_3$ is hydrogen, halo, alkyl of from 1 to 6 carbon atoms, methoxy, phenyl, trifluoromethyl, 2,5-dichloro, 2,5-dimethyl, 2,3,5-trimethyl, carboxylic acyl of from 1 to 6 carbon atoms, alpha-hydroxyalkyl of from 1 to 6 carbon atoms, 2-chlorophenyl, 4-chlorophenyl, 2,4-dichlorophenyl, 4-methoxyphenyl, 2-tolyl, 4-tolyl or

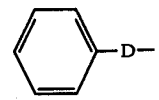

wherein D is $O, CO, S, SO, SO_2, CH_2$, or CHOH; provided that $R_3$ may not be hydrogen when X and Y are oxygen, m and m' are 2; $R_1$ and $R_2$ are $CH_3$, and R is $CO_2H$; and when R is COOH, the pharmaceutically acceptable salts thereof.

32. A method of treating arteriosclerosis in a mammal in need of such treatment which method comprises administering to said mammal an anti-arteriosclerotic effective amount of a composition as claimed in claim 31.

* * * * *